(12) United States Patent
Bracht et al.

(10) Patent No.: US 7,560,121 B1
(45) Date of Patent: Jul. 14, 2009

(54) TRANSDERMAL THERAPEUTIC SYSTEM WITH A HIGHLY EFFECTIVE NEUROLEPTIC AGENT

(75) Inventors: Stefan Bracht, Ochtendung (DE); Michael Horstmann, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1133 days.

(21) Appl. No.: 09/959,201

(22) PCT Filed: Apr. 7, 2000

(86) PCT No.: PCT/EP00/03113

§ 371 (c)(1),
(2), (4) Date: Dec. 19, 2001

(87) PCT Pub. No.: WO00/64419

PCT Pub. Date: Nov. 2, 2000

(30) Foreign Application Priority Data

Apr. 22, 1999 (DE) ................. 199 18 105

(51) Int. Cl.
*A61L 15/16* (2006.01)
*A61M 37/00* (2006.01)

(52) U.S. Cl. ..................................... 424/449
(58) Field of Classification Search ........... 424/448, 424/449, 484, 486, 400, 443, 488, 947
See application file for complete search history.

(56) References Cited

U.S. PATENT DOCUMENTS

| 5,120,545 | A | 6/1992 | Ledger et al. |
| 5,474,783 | A | 12/1995 | Miranda et al. |
| 5,882,676 | A * | 3/1999 | Lee et al. .................... 424/449 |
| 5,891,461 | A | 4/1999 | Jona et al. |
| 6,228,875 | B1 * | 5/2001 | Tsai et al. ................... 514/380 |

FOREIGN PATENT DOCUMENTS

| DE | 39 10543 A1 | 10/1990 |
| EP | A1-0156080 | 10/1985 |
| EP | 0 314 528 A1 | 10/1987 |
| EP | 0 452 837 A2 * | 10/1991 |
| EP | A2-0452837 | 10/1991 |
| WO | WO 93/00058 | 1/1993 |
| WO | WO 97/29735 | 8/1997 |

OTHER PUBLICATIONS

Viogt, R., Pharmazeutische Technologie fur Studium und Beruf, 7. Edition, Chapter 16.2.1.2 and 26.4.3.3.5, pp. 591-596, (1993).
Mutschler E.: Arzneimittelwirkungen, 6. Aufl., Wissenschaftliche Verlagsgesellschaft, Stuttgart 1991.
Rote Liste Win 1999/I Vers. 2.7, Rote Liste Service GmbH, ECV Editio Canto Verlag.
Koytchev R. et al.: "Absolute Bioavailability of Oral Immediate and Slow Release Fluphenazine in Healthy Volunteers", Eur. J. Clin. Pharmacol 1996; 51: 183-187.
Monographie: "Phenothiazin" in The Merck Index, 12th Edition 1996.

* cited by examiner

*Primary Examiner*—Michael G Hartley
*Assistant Examiner*—Jagadishwar R Samala
(74) *Attorney, Agent, or Firm*—Birch Stewart Kolasch & Birch LLP

(57) ABSTRACT

A transdermal therapeutic system consisting of a backing layer, at least one active substance-containing matrix layer, which may at the same time possess pressure-sensitive adhesive properties, as well as a removable protective layer is characterized by a content of a neuroleptic, a content of at least one permeation enhancer as well as by a layer which is pressure-sensitive adhesive on the skin-facing side and based on polymers which are pure hydrocarbons.

15 Claims, 4 Drawing Sheets

TRANSDERMAL THERAPEUTIC SYSTEM WITH A HIGHLY EFFECTIVE NEUROLEPTIC AGENT

This application is the national phase under 35 U.S.C. § 371 of PCT International Application No. PCT/EP00/03113 which has an International filing date of Apr. 7, 2000, which designated the United States of America.

BACKGROUND OF THE INVENTION

1. Field of the Invention

The invention pertains to a layered transdermal therapeutic system that contains fluphenazine, flupentixol or triflupromazine.

2. Description of the Related Art

Fluphenazine is a tricyclic, very potent neuroleptic from the group of perphenazines. These substances possess antipsychotic action—especially in cases of schizophrenic psychoses—without substantially affecting consciousness and intellectual faculties. The typical oral daily dose is 3-6 mg, under the conditions of hospital treatment up to 24 mg (cf. Mutschler E. "Axzneimittelwirkungen", 6th edition, Wissenschaftliche Verlagsgesellschaft Stuttgart 1991).

The half-life in blood plasma is 15 h. For intravenous therapy, ester forms, e.g. decanoate and enantate, are available, each having markedly prolonged half-lifes. In oral therapy the dihydrochloride of fluphenazine is used (cf. Rote Liste Win 1997/II Vers. 2.4, ROTE LISTE Service GmbH, ECV Editio Cantor Verlag).

Therapeutic treatment of patients suffering from schizophrenic psychoses typically requires chronic, often life-long, administration of appropriate medicaments. Frequently, patients are only partly or temporarily responsive, so that active cooperation in the therapy can frequently not be achieved. Consequently, independent intake by the patient is afflicted with great uncertainties.

SUMMARY OF THE INVENTION

The object of the invention is thus to provide a fluphenazine-containing transdermal therapeutic system (TTS) which releases at least 1 µg/cm²·d of active agent to the human skin, thus replacing oral intake of once or even several times a day by an application of 1 to 3 times a week.

The problem can be solved in that the TTS comprises an enhancer and has a skin-facing pressure-sensitive adhesive layer based on polymers which are pure hydrocarbons.

DETAILED DESCRIPTION

Figure 1:
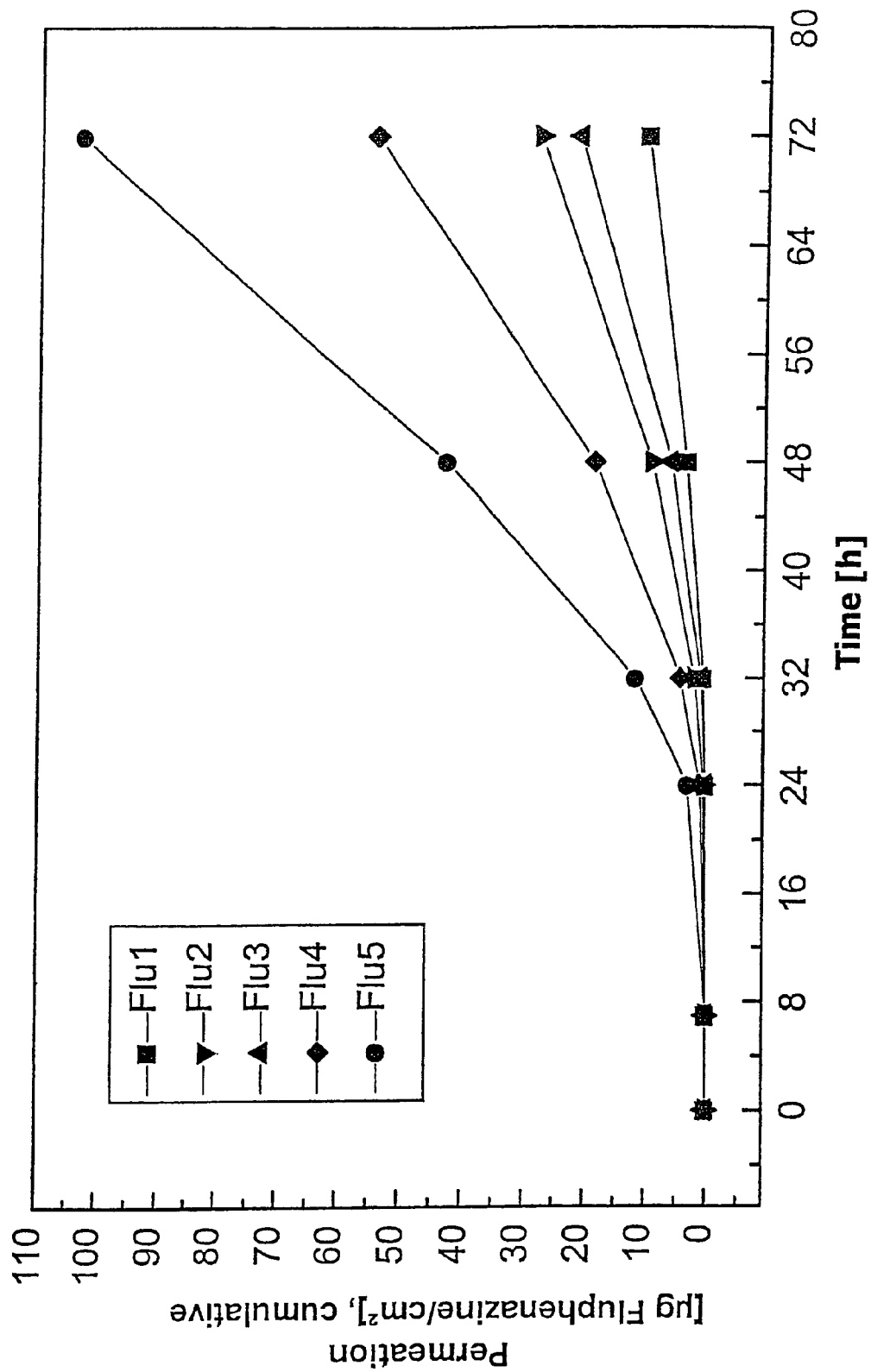
FIG. 1 is a graph showing the permeation of Examples Flu1-Flu5.

What heretofore stood in the way of the development of corresponding transdermal therapeutic systems was the presumption that the skin permeability for fluphenazine and, in particular, its salts is only very low.

For fluphenazine dihydrochloride one has thus to expect poor permeability in human skin owing to the salt structure and the hydrophilia connected therewith. To compound matters there is the relatively high molecular weight of 437,53 Da as well as the sterically fixed tricycle in the molecule.

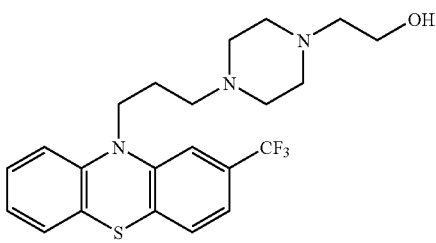

The transdermal absorption of several milligrams a day, on an acceptable application surface of maximally 50 cm², thus meets with certain reservations.

As a consequence no descriptions of transdermal systems meeting the demands of practice and having systemic action can be found in the literature.

Rather, the patent literature refers to fluphenazine only where TTSs having certain physicochemical properties (U.S. Pat. No. 5,474,783) or additives (U.S. Pat. No. 5,120,545) are described, without establishing a relation to concrete embodiment examples for this active substance. These patent specifications contain fluphenazine merely as one possible active agent from a purely theoretic list of conceivable active agents.

More recent examinations on the pharmacokinetics of fluphenazine after oral administration have been published (Koytchev R et al.: "Absolute Bioavailability of oral immediate and slow release fluphenazine in healthy volunteers", Eur. J. Clin. Pharmacol. 1996; 51: 183-187). The results show that only 2.5 to 3.5% of the orally administered dose of fluphenazine becomes available in the blood.

For direct administration into the blood stream avoiding the digestive tract and the first-pass effect in the liver, as possible via the transdermal route, it would thus be sufficient to use a fraction of the oral dose typically applied.

A typical transdermal daily dose should be expected to amount from 90 to 180 µg, under hospital conditions up to 840 µg.

All examinations were carried out with fluphenazine dihydrochloride (ICN Biomedicals Inc. Ohio, USA). This substance form is being used for therapeutic purposes worldwide so that, in contrast to the free base, there are extensive toxicological and regulatory dossiers available.

Skin permeability was examined in vitro using full thickness cow udder skin and human epidermis, the latter having been separated from human full-thickness skin by heat separation.

The tests were carried out at 32° C. in a suitable permeation device (modified Franz cell), and fluphenazine was measured in the resultant samples using a suitable HPLC method. All indicated values are based on n=3 samples.

Within the framework of matrix or drug-in-adhesive technology, pressure-sensitive adhesive films based on poly(meth)acrylates were examined as matrices initially.

These were the market products Durotak 387-2051, Durotak 387-2287 and Durotak 387-2353 (National Starch and Chemical Co.).

Due to their being well tolerated by the skin and their low allergising potential, such pressure-sensitive adhesives are widely used in medicinal products.

The dihydrochloride salt is almost insoluble in such polymers or in the organic solvents required for processing. Addition of Eudragit E100 (Röhm Pharma GmbH) was therefore provided for in all cases. This poly-(meth)acrylate has trialkylamino groups in its lateral chain and is capable of functioning as an ion-exchange resin. In this way, the chloride ions of the fluphenazine dihydrochloride are bonded to Eudragit E100 while protons are accepted simultaneously, with fluphenazine being formed as a free base in a certain equilibrium. Advantageous is an at least equimolar ratio of Eudragit E100 and fluphenazine dihydrochloride, i.e. of amounts by weight having the same equivalent weight calculated as potassium hydroxide.

With this procedure a surprisingly high solubility of at least 15%-wt. of fluphenazine dihydrochloride in Durotak 387-2051 was found; for Durotak 387-2287 still at least 10%-Wt.

Nevertheless, the permeation rate results on cow udder skin were very low (Examples Flu1-Flu5, see FIG. 1, cf. Table 1).

The carboxyl group-free Durotak 387-2287 (cf. Example Flu5), however, proved clearly superior to the carboxyl group-containing 387-2051 (cf. Examples Flu3 and Flu5). Due to their ability to form salts with fluphenazine base, carboxyl groups are obviously detrimental to fluphenazine release. This assumption could be confirmed by neutralizing Durotak 387-2051, under otherwise equal conditions, with an equimolar amount of potassium hydroxide (cf. Example Flu2 and Flu4). This r suited in increased permeation values, which did, however, still not come up to those of the neutral Durotak 387-2287.

Overall, the results for adhesive matrices based on poly (meth)acrylates show high solubility of fluphenazine with simultaneous poor release.

Consequently, in particular the quantitative potential efficiency of the active substance contained is very poor.

Figure 2:
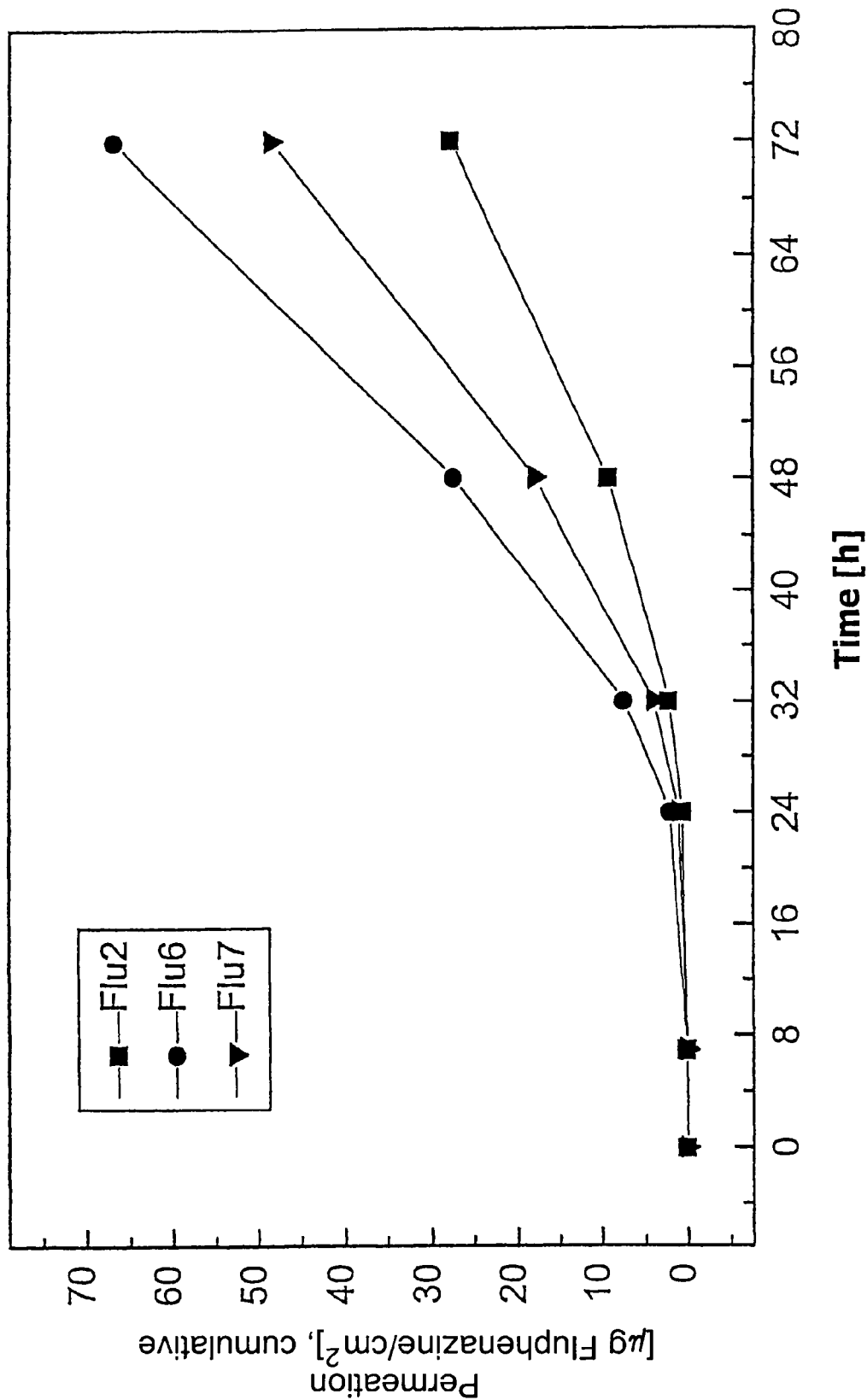
FIG. 2 is a graph showing the permeation of Examples Flu2, Flu6 and Flu 7.
Figure 3:
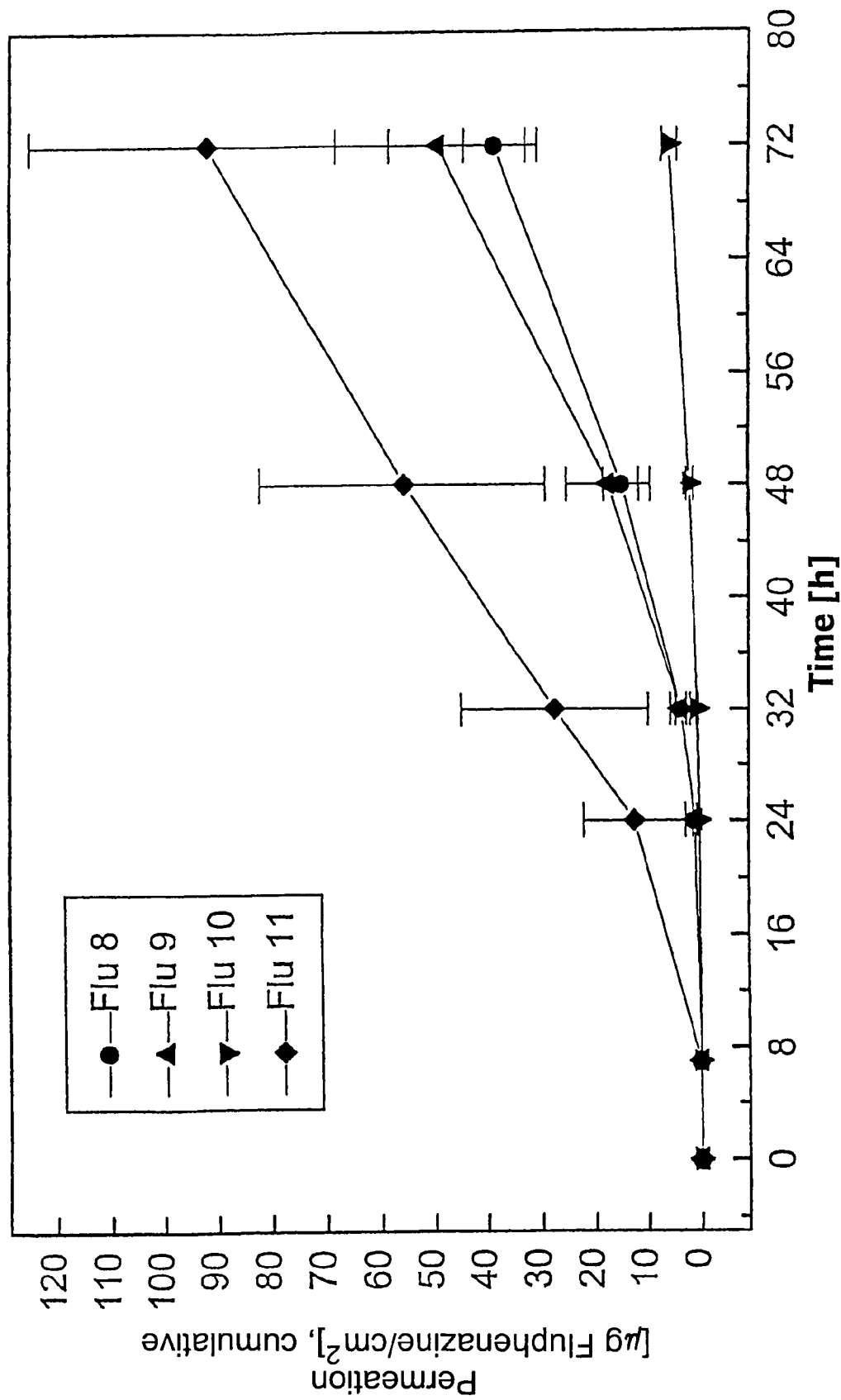
FIG. 3 is a graph showing the permeation of Examples Flu8-Flu11.

This could surprisingly be improved by additives. Both by addition of the fatty alcohol 2-octyl dodecanol (Eutanol® G) and by addition of the fatty acid oleic acid it was possible to markedly increase the permeation through cow udder skin (see FIG. 2. cf. Table 2).

Especially the fatty acid clearly shows positive effects, which may be due to ion pair formation with fluphenazine base. The good skin permeability of such ion pair complexes is known to those skilled in the art.

While thus the use of a basic auxiliary substance such as Eudragit E100 with simultaneous use of an acid auxiliary substance such as oleic acid yields clear advantages, pressure-sensitive adhesives based on poly(meth)acrylate appear to be poorly suitable as matrices.

The principle developed was therefore applied to other possible adhesive matrices.

Surprisingly, it was found that a polymer matrix based on pure hydrocarbons (Oppanol B10 and B100) leads to very highly improved permeation rates through cow udder skin (see F cf. Table 3).

In particular in early stages of the experiment, after 24 and 32 hours, a considerable advantage over comparative matrices becomes apparent.

The pressure-sensitive adhesive formulation based on pure hydrocarbon polymers thus shows clear advantages over poly (meth)acrylates and surprisingly also over a silicone adhesive (BioPSA Q7-4301, Dow Corning Chem. Co.).

Especially the ratio of active substance load (now only 5%-wt.) to active substance permeation and thus the potential efficiency have improved considerably.

In a further experiment the optimised formulation was finally tested on human epidermis. The data obtained show an excellent course of permeation with a short lagtime and almost linear characteristic (see FIG. 4).

Optimal results were achieved with an equimolar ratio of fluphenazine, Eudragit E100 and oleic acid (relative to the respective equivalent weights, calculated as potassium hydroxide.).

Figure 4:
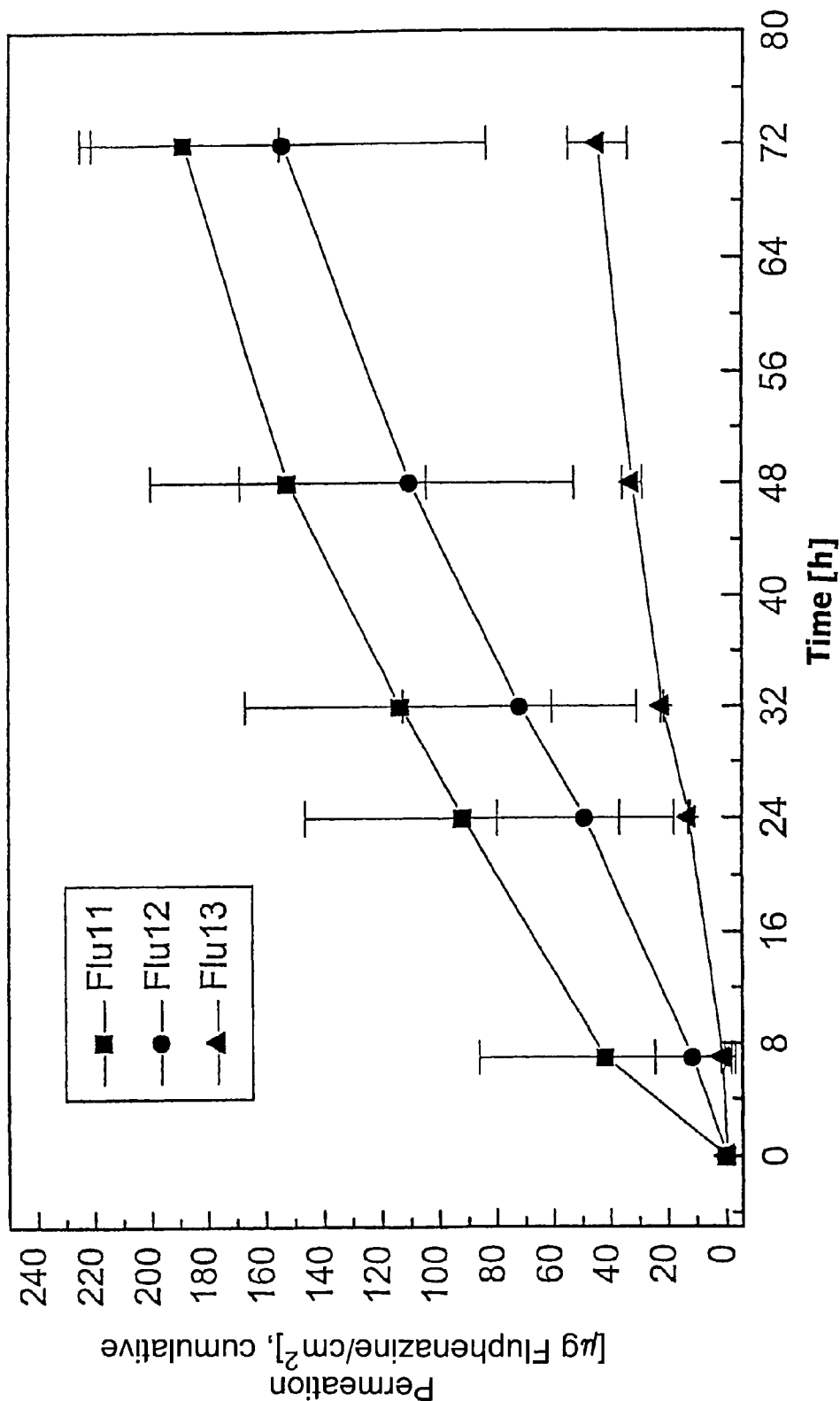
FIG. 4 is a graph showing the permeation of Examples Flu11-Flu13.

Both increasing the proportion of oleic acid and of Eudragit E100 lead to poorer results in each case (see FIG. 4, cf. Table 4).

Maximum flow rates of 2.9 µg/h·cm$^2$ of fluphenazine base were achieved.

It would thus be possible to achieve the expected transdermal daily dose of 90 to 180 µg of fluphenazine (see above) already with a TTS having a size of only 2 to 4 cm$^2$. Even the amount of 840 µg per day, which might be required in hospital treatment, could be achieved transdermally with a system of less than 20 cm$^2$.

On the basis of these data the transdermal therapy with fluphenazine has become possible. Within the framework of the invention even surprisingly small TTSs are possible.

The invention enables the transdermal therapy with fluphenazine at a dosage which is far below the amounts required for oral administration. Transdermal therapy with fluphenazine is not only an alternative administration form but, due to its greater dose-related efficiency, also offers advantages over common oral long-term therapy.

Due to the great chemical similarity, the equivalent pharmacodynamic action, the comparable therapeutic doses necessary, and the expected similarity of the pharmacokinetics, the invention also applies to further active substances as follows:

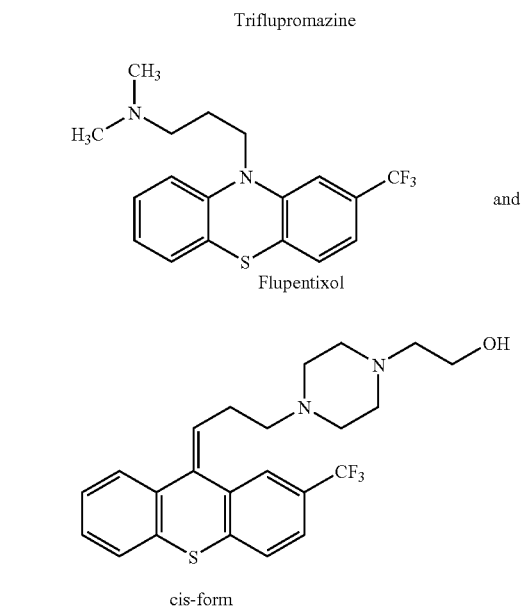

In the case of flupentixol the cis-isomer (α-flupentixol) is to be preferred because of its greater pharmacodynamic potency.

The invention thus relates, in particular, to transdermal therapeutic systems consisting of a backing layer, at least one active substance-containing matrix layer, which may at the same time possess pressure-sensitive adhesive properties, as well as a removable protective layer, by means of which systems there is achieved a release rate to human skin of at least 1 µg/cm²·d of a neuroleptic selected from the group comprising fluphenazine, flupentixol and triflupromazine.

The invention further relates to a process for administering a highly potent neuroleptic to a person requiring treatment with such active substance, said active substance being fluphenazine and being r leased at a rate of at least 1 µg/cm²·d to the human skin. In a corresponding manner and at the rate mentioned it is also possible to use such process for releasing the active substances flupentixol or triflupromazine to the human skin.

The transdermal therapeutic systems according to the invention can thus be used for administering a strongly potent neuroleptic, selected from the group comprising fluphenazine, flupentixol and triflupromazine, to a person in need of treatment with such active substance.

The process according to the invention for administering the above-mentioned neuroleptics and the use of the TTSs according to the invention for administering these neuroleptics are particularly advantageous in the treatment of patients suffering from psychoses or schizophrenic psychoses. As mentioned at the beginning, it is in particular in the case of such patients—who mostly require long-term drug treatment—that oral administration of medicaments involves disadvantages.

In the following, further demands made on a TTS will be pointed out:

Because of the known photoreactivity of the phenothiazine backbone it may be necessary to use stabilizing additives. Apart from UV radiation-absorbing substances or pigments these are especially antioxidants. Preferred antioxidants are ascorbyl palmitate, vitamin E and its pharmaceutically acceptable esters such as butyl hydroxyanisole (BHA) and butyl hydroxytoluol (BHT). Also, sulphur-containing stabilizers such as methionine or inorganic sulfites may be necessary. The use of hexamethylenetetramine (methenamine) as specific stabilizer for phenothiazin is possible too (see monography "Phenothiazine" in The Merck Index, 12th edition 1996).

Such substances are typically added to the active substance-containing matrix of the TTS in a concentration of below 1%-wt.

In view of the light sensitivity it may further be useful to use a film or sheet which has been rendered light-permeable by pigmentation, lacquering or metallization, or by a corresponding composite of materials.

EXAMPLES 1 TO 13

The example formulations Flu1 to Flu13 were prepared under the general conditions as described hereinbelow:

The various Durotak adhesives and the silicone adhesive were used in the form of solutions in organic solvents as delivered by the manufacturer.

Eudragit E100 was processed in the form of a solution in ethyl acetate (60%-wt.).

The mixture of 75 parts by weight of Oppnaol B10 with 25 parts by weight of Oppanol B100 was used as a solution in special boiling point gasoline 80-110 (31%-wt.).

The neutralization of carboxyl group-containing polyacrylate adhesives (Durotak 387-2051 and 387-2353) was effected by reacting these solutions of adhesive with potassium hydroxide in methanolic solution (10%-wt.). The amount of potassium hydroxide used corresponded to the lower limit of the potassium hydroxide number (mg KOH/g polymer) specified by the manufacturer for the respective product.

The indicated amount of fluphenazine dihydrochloride (fluphenazine 2 HCl) was initially mixed with the Eudragit solution before the pressure-sensitive adhesive solutions and, finally, if required, further components were incorporated. Where dilution of the mass to a suitable viscosity was necessary, this was done with ethyl acetate.

The homogenous-stirred mass was coated onto a 100-µm-thick film of siliconized polyethylene therephthalate (PET) employing a beam applicator unit, and subsequently dried in a drawing-off air oven at 80° C. for 5 minutes. The dried adhesive film was covered with a PET film (15 µm in thickness) as a protective film.

The weight per unit area of the adhesive matrix was adjusted to be in all cases 80 g/m², by appropriate selection of the coating thickness.

The compositions of the example formulations listed in the following tables relate to the dried active substance-containing layer of the TTS (Table 1 to 4).

TABLE 1

Composition of the pressure-sensitive adhesive matrix layer in percent by weight:

| Components | Example Flu1 | Example Flu2 | Example Flu3 | Example Flu4 | Example Flu5 |
|---|---|---|---|---|---|
| Fluphenazine 2 HCl | 11.7 | 11.7 | 17.6 | 17.6 | 11.7 |
| Eudragit E100 | 14.3 | 14.3 | 21.5 | 21.5 | 14.3 |
| Durotak 387-2051 | 74.0 | — | 39.1 | — | — |
| Durotak 387-2051 Potassium salt* | — | 74.0 | — | 39.1 | — |
| Durotak 387-2287 | — | — | — | — | 74.0 |
| Total | 100.0 | 100.0 | 100.0 | 100.0 | 100.0 |

TABLE 2

Composition of the pressure-sensitive adhesive matrix layer in percent by weight:

| Components | Example Flu6 | Example Flu7 |
|---|---|---|
| Fluphenazine 2 HCl | 11.7 | 11.7 |
| Eudragit E100 | 14.3 | 14.3 |
| Oleic Acid | 6.5 | — |
| Eutanol G | — | 5.0 |
| Durotak 387-2051 Potassium salt* | 67.5 | 69.0 |
| Total | 100.0 | 100.0 |

TABLE 3

Composition of the pressure-sensitive adhesive matrix layer in percent by weight:

| Components | Example Flu8 | Example Flu9 | Example Flu10 | Example Flu11 |
|---|---|---|---|---|
| Fluphenazine 2 HCl | 5.83 | 5.83 | 5.83 | 5.83 |
| Eudragit E100 | 7.15 | 7.15 | 7.15 | 7.15 |
| Oleic acid | 3.22 | 3.22 | 3.22 | 3.22 |
| Eutanol G | — | — | 20.0 | — |

TABLE 3-continued

Composition of the pressure-sensitive adhesive matrix layer in percent by weight:

| Components | Example Flu8 | Example Flu9 | Example Flu10 | Example Flu11 |
|---|---|---|---|---|
| Bio PSA Q7-4301 | 83.8 | — | — | — |
| Durotak 387-2287 | — | 83.8 | 63.8 | — |
| Durotak 387-2353 Potassium salt* | — | — | — | — |
| Oppanol B10/B100 75 + 25* | — | — | — | 83.8 |
| Total | 100.0 | 100.0 | 100.0 | 100.0 |

TABLE 4

Composition of the pressure-sensitive adhesive matrix layer in percent by weight:

| Components | Example Flu 12 | Example Flu13 |
|---|---|---|
| Fluphenazine 2 HCl | 5.83 | 5.83 |
| Eudragit E100 | 10.7 | 7.15 |
| Oleic acid | 3.22 | 4.83 |
| OppanolB10/B100 75 + 25* | 80.3 | 82.2 |
| Total | 100.0 | 100.0 |

The invention claimed is:

1. A transdermal therapeutic system consisting essentially of:
   a) a backing layer,
   b) at least one active substance-containing polymer matrix layer, which has or has not at the same time pressure sensitive adhesive properties;
   c) at least one permeation enhancer;
   d) at least one basic auxiliary substance which is a basic polymer; and
   e) a pressure-sensitive adhesive layer on a skin-facing side of the matrix layer in case the matrix layer does not have pressure-sensitive adhesive properties;
   wherein the active substance is at least one neuroleptic selected from the group consisting of a pharmaceutically acceptable salt of fluphenazine, a pharmaceutically acceptable salt of flupentixol and a pharmaceutically acceptable salt of triflupromazine, wherein the permeation enhancer is selected from the group consisting of saturated fatty acids, mono-unsaturated fatty acids, saturated fatty alcohols and unsaturated fatty alcohols, each having 6 to 18 carbon atoms, and
   wherein said polymer matrix layer having pressure sensitive adhesive properties and said pressure sensitive adhesive respectively are based on polymers comprising pure hydrocarbons.

2. The transdermal therapeutic system according to claim 1, wherein the active substance concentration in the matrix layer is between 0.5 and 5.0%-wt.

3. The transdermal therapeutic system according to claim 1, wherein the pharmaceutically acceptable salt of the active substance is a hydrochloride salt or a dihydrochloride salt.

4. The transdermal therapeutic system according to claim 1, wherein the basic auxiliary substance is in an amount corresponding to 0.5 to 1.5 times the equivalent weight of the active substance amount contained, expressed as potassium hydroxide.

5. The transdermal therapeutic system according to claim 4, wherein the basic auxiliary substance is a copolymer of dimethylaminoethyl methacrylate and methacrylate units.

6. The transdermal therapeutic system according to claim 1, wherein the permeation enhancer is selected from the group consisting of undecylenic acid, lauric acid, myristic acid and oleic acid.

7. The transdermal therapeutic system according to claim 1, wherein the permeation enhancer is selected from the group consisting of 1-decanol, 1 dodecanol, oleyl alcohol and 2-octyl dodecanol.

8. The transdermal therapeutic system according to claim 1, wherein the permeation enhancer is selected from the group consisting of fatty alcohols, polyoxyethyl ethers, fatty acid methyl esters, fatty acid ethyl esters, fatty acid isopropyl esters and fatty alcohol fatty acid esters.

9. The transdermal therapeutic system according to claim 1, wherein the pressure-sensitive adhesive layer on the skin-facing side consists essentially of at least two polymers having the same molecular structure, but differing in their mean molecular weight.

10. The transdermal therapeutic system according to claim 1, which further comprises an additive that is at least one stabilizer selected from the group consisting of antioxidants and hexamethylenetetramine contained in an amount of 0.01 to 1.0%-wt. in the pressure-sensitive adhesive layer.

11. A method of treating a patient suffering from psychoses or schizophrenic psychoses, which comprises administering to the patient in need thereof a transdermal therapeutic system according to claim 1.

12. The transdermal therapeutic system according to claim 1, wherein a release rate is approximately 5 $\mu g/cm^2$ ·day or higher.

13. The transdermal therapeutic system according to claim 1, wherein a release rate is at least 1 $\mu g/cm^2$·day.

14. The transdermal therapeutic system according to claim 1, wherein said system additionally comprises at least one additive selected from the group consisting of stabilizers and tackifiers.

15. The transdermal therapeutic system according to claim 1, wherein said polymer matrix layer having pressure-sensitive adhesive properties and said pressure-sensitive adhesive respectively are substantially non-aqueous.

* * * * *